United States Patent
Kantzer et al.

(10) Patent No.: US 10,975,017 B2
(45) Date of Patent: Apr. 13, 2021

(54) PROCESS FOR MANUFACTURING ETHYLENE AMINES

(71) Applicant: NOURYON CHEMICALS INTERNATIONAL B.V., Arnhem (NL)

(72) Inventors: Eike Nicolas Kantzer, Uddevalla (SE); Karl Fredrik Lake, Södertälje (SE); Antoon Jacob Berend Ten Kate, Arnhem (NL); Michiel Jozef Thomas Raaijmakers, Deventer (NL); Rens Veneman, Deventer (NL); Ina Ehlers, Stenungsund (SE); Michael Bertil Einar Sarning, Gothenburg (SE); Hendrik Van Dam, Ede (NL); Rolf Krister Edvinsson, Partille (SE); Jenny Valborg Therese Adrian Meredith, Årsta (SE)

(73) Assignee: NOURYON CHEMICALS INTERNATIONAL B.V., Arnhem (NL)

(*) Notice: Subject to any disclaimer, the term of this patent is extended or adjusted under 35 U.S.C. 154(b) by 0 days.

(21) Appl. No.: 16/468,514

(22) PCT Filed: Dec. 12, 2017

(86) PCT No.: PCT/EP2017/082394
§ 371 (c)(1),
(2) Date: Jun. 11, 2019

(87) PCT Pub. No.: WO2018/108890
PCT Pub. Date: Jun. 21, 2018

(65) Prior Publication Data
US 2019/0308930 A1    Oct. 10, 2019

(30) Foreign Application Priority Data
Dec. 15, 2016   (EP) .................................. 16204362

(51) Int. Cl.
*C07C 209/16* (2006.01)
*C07C 211/14* (2006.01)
*C07D 233/36* (2006.01)
*C07C 209/62* (2006.01)

(52) U.S. Cl.
CPC .......... *C07C 209/16* (2013.01); *C07C 209/62* (2013.01); *C07C 211/14* (2013.01); *C07D 233/36* (2013.01)

(58) Field of Classification Search
CPC ... C07C 209/16; C07C 209/62; C07C 211/14; C07D 233/36
See application file for complete search history.

(56) References Cited

U.S. PATENT DOCUMENTS

| 2,448,767 | A | | 9/1948 | Calson |
| 3,383,417 | A | | 5/1968 | Lichtenwalter et al. |
| 3,682,919 | A | | 8/1972 | Johansson et al. |
| 4,044,053 | A | | 8/1977 | Brennan et al. |
| 4,503,250 | A | * | 3/1985 | Herdle .................. C07C 209/16 564/479 |
| 5,225,599 | A | | 7/1993 | King et al. |
| 6,534,441 | B1 | | 3/2003 | Bartley et al. |
| 7,700,806 | B2 | | 4/2010 | van Cauwenberge et al. |
| 8,563,778 | B2 | * | 10/2013 | Hanson .................. C07C 209/16 564/475 |
| 9,353,044 | B2 | * | 5/2016 | King ..................... B01J 37/0201 |
| 2009/0240084 | A1 | | 9/2009 | van Cauwenberge et al. |
| 2012/0232309 | A1 | | 9/2012 | Schaub et al. |
| 2019/0031597 | A1 | * | 1/2019 | Edvinsson ............. C07C 269/06 |
| 2019/0039993 | A1 | * | 2/2019 | Edvinsson ........ C07C 273/1854 |

(Continued)

FOREIGN PATENT DOCUMENTS

| CA | 2801109 A1 * 12/2011 .......... B01J 31/2414 |
| CN | 102167682 A   8/2011 |

(Continued)

OTHER PUBLICATIONS

Applicant letter to ISA concerning earlier search ('PCT Direct') (Dec. 12, 2017) (Year: 2017).*
English-Language Machine Translation CN 103333323 A (2013) (Year: 2013).*
English-Language Machine Translation JP 2815477 B (1998) (Year: 1998).*
English-Language Machine Translation JP 2008002018 A (2008) (Year: 2018).*
English-Language Machine Translation JP 2008019520 A (2008) (Year: 2008).*

(Continued)

*Primary Examiner* — Alexander R Pagano
(74) *Attorney, Agent, or Firm* — Lorenz & Kopf, LLP

(57) ABSTRACT

A process for preparing polyethyleneamines of formula NH2-(CH2-CH2-NH-)pH wherein p is at least 3 and wherein one or more —NH-CH2-CH2-NH— units may be piperazine units and/or ethylene urea derivatives of these compounds, includes reacting monoethylene glycol with an amine-functional compound having at least two —NH— units, of which at least one is selected from primary amine groups and cyclic secondary amine groups, in the presence of a carbon oxide-delivering agent. The amine-functional compound includes at least one —NH-CH2-CH2-NH— unit, and one or more —NH-CH2-CH2-NH— units may be in the form of cyclic ethylene urea moieties, piperazine moieties, or linear ethylene urea moieties. The molar ratio of amine-functional compound to monoethylene glycol is above 1.2:1 and the molar ratio of carbon oxide delivering agent to —NH-CH2-CH2-NH— units is at least 0.5:1. The process makes it possible to obtain ethylene amines and derivatives thereof without using ammonia or metal-containing catalysts.

20 Claims, No Drawings

(56) References Cited

U.S. PATENT DOCUMENTS

| | | | | |
|---|---|---|---|---|
| 2019/0039994 A1* | 2/2019 | Edvinsson | ............ | C07C 209/62 |
| 2019/0047971 A1* | 2/2019 | Edvinsson | ............ | C07D 295/13 |
| 2019/0308930 A1* | 10/2019 | Kantzer | ................ | C07C 209/62 |
| 2020/0131136 A1* | 4/2020 | Ten Kate | ............... | C07C 209/16 |
| 2020/0165187 A1* | 5/2020 | Ten Kate | ............... | C07C 209/62 |
| 2020/0165207 A1* | 5/2020 | Kantzer | ................ | C07C 209/78 |
| 2020/0165212 A1* | 5/2020 | Raaijmakers | ........ | C07D 233/34 |
| 2020/0199060 A1* | 6/2020 | Ten Kate | ............... | C07C 209/62 |
| 2020/0207701 A1* | 7/2020 | Veneman | .............. | C07C 209/16 |

FOREIGN PATENT DOCUMENTS

| | | | | | |
|---|---|---|---|---|---|
| CN | 103333323 | A | | 10/2013 | |
| CN | 103333323 | B | * | 9/2015 | |
| EP | 040709 | A1 | | 1/1991 | |
| JP | 2815477 | B2 | * | 10/1998 | |
| JP | 2008002018 | A | * | 1/2008 | |
| JP | 2008019520 | A | * | 1/2008 | |
| WO | 9115458 | A1 | | 10/1991 | |
| WO | WO-2011151268 | A1 | * | 12/2011 | ......... C08G 73/0206 |
| WO | WO-2017125358 | A1 | * | 7/2017 | ......... C07D 403/06 |
| WO | 2018108888 | A1 | | 6/2018 | |

OTHER PUBLICATIONS

English-Language Machine Translation WO 2017125358 A (2017) (Year: 2017).*
CAS Abstract WO 2011/151268 (2011) (Year: 2011).*
CAS Abstract WO 2017125358 (2017) (Year: 2017).*
CAS Abstract Ethylene Glycol (1984) (Year: 1984).*
CAS Abstract JP 2008002018 (2008) (Year: 2008).*
CAS Abstract JP 2008019520 (2008) (Year: 2008).*
STN abstract of King et al. Patent (U.S. Pat. No. 5,225,599) (Year: 1993).
EPO, Extended European Search Report issued in EP Application No. 162043624 , dated Jul. 21, 2017.
EPO, International Search Report issued in International Application No. PCT/EP20171082394, dated Feb. 20, 2018.
Schweitzer, C.E., "Ethyleneurea. II. Syntheses From Ethylene Glycol or Ethanolamine and Urea (or Carbon Dioxide and Ammonia)", Journal of Org. Chem., 1950, pp. 475-480, vol. 15, No. 3.
Database WPI, Week 201410, Thomson Scientific, London, GB; AN 2013-W87652, XP002770988.

* cited by examiner

PROCESS FOR MANUFACTURING ETHYLENE AMINES

This application is a national stage filing under 35 U.S.C. § 371 of PCT/EP2017/082394, filed Dec. 12, 2017, which claims priority to European Patent Application No. 16204362.4, filed Dec. 15, 2016, the contents of which are each incorporated herein by reference in their entireties.

The present invention pertains to a method for manufacturing ethylene amines using a specific starting material.

Reductive amination of monoethanolamine (MEA) in the presence of ammonia to form ethylene diamine is a well-known commercially applied process.

It would be expected that this reductive amination technology could also be effectively applied to convert 1,2-ethanediol, also known as monoethylene glycol or ethylene diol. However, it has been found that this is not the case.

U.S. Pat. No. 7,700,806 describes a process for preparing ethylene amines and ethanol amines by hydrogenative amination of monoethylene glycol and ammonia in the presence of a catalyst. The process is carried out in two stages, wherein in the first stage the amination is carried out over a hydroamination catalyst to a monoethylene glycol conversion of not more than 40%, and in the second stage the reaction is carried out over a supported catalyst comprising ruthenium and cobalt, with a specific particle shape.

US 2012/0232309 describes preparing a primary amine by reacting an alcohol with ammonia and elimination of water, wherein in a homogeneously catalyzed reaction, a mixture of alcohol, ammonia, nonpolar solvent, and a specific catalyst is reacted to obtain a product mixture.

Ethylene amines, in particular diethylene triamine (DETA), and higher ethylene amines such as triethylene tetramine (TETA) are attractive products from a commercial point of view. Monoethylene glycol, also known as 1,2-ethanediol, is an attractive starting material in the chemical industry, also because it can be derived from renewable resources. There is therefore need in the art for a process which allows the conversion of monoethylene glycol to ethylene amines. It is preferred for such a process to have a high yield. It is also preferred if such a process can be carried out without using ammonia, or metal-containing catalysts. The present invention provides such a process.

The invention pertains to a process for preparing polyethyleneamines of the formula $NH_2$-$(CH_2$-$CH_2$-$NH$-$)_pH$ wherein p is at least 3. wherein one or more —$NH$-$CH_2$-$CH_2$-$NH$— units may be present as piperazine units and/or ethylene urea derivatives of these compounds, comprising the step of reacting monoethylene glycol with an amine-functional compound comprising at least two —NH— units of which at least one is selected from the group of primary amine groups and cyclic secondary amine groups, in the presence of a carbon oxide-delivering agent, the amine-functional compound comprising at least one —$NH$-$CH_2$-$CH_2$-$NH$— unit, wherein one or more —$NH$-$CH_2$-$CH_2$-$NH$— units in the amine-functional compound may be present in the form of cyclic ethylene urea moieties, piperazine moieties, or linear ethylene urea moieties, wherein the molar ratio of amine-functional compound to monoethylene glycol is above 1.2:1 and the molar ratio of carbon oxide-delivering agent to —$NH$-$CH_2$-$CH_2$-$NH$— units in the amine-functional compound is at least 0.5:1.

It has been found that the process according to the invention makes it possible to obtain ethylene amines and derivatives thereof via a process which makes use of an attractive starting material, with relatively high yield, without having to use ammonia or metal-containing catalysts. Further advantages of the process according to the invention and specific embodiments thereof will become apparent from the further specification.

It is noted that U.S. Pat. No. 4,503,250 describes a process for preparing predominantly linear polyalkylene polyamines by reacting ammonia or an alkylene amine compound having two primary amine groups with an alcohol or an alkanol amine in the presence of a derivative of carbonic acid at a temperature at which the reaction will proceed under pressures sufficient to maintain the reaction mixture in the liquid phase. This reference states that it is possible to use alcohols. However, all examples make use of ethanolamine compounds, specifically monoethanolamine, diethanolamine, and aminoethylethanolamine. The only di-alcohol compound is diethanolamine (DEA), which is reacted with urea and only results in the formation of trace amounts of L-TETA (0.7 wt. %). It results mainly in the conversion of the ethanol group into an amine group, which is not the aim of the present invention.

Further, this document indicates that the amount of CO is not critical. The compound is regarded as a catalyst. This can also be seen from the very low amounts used in the examples. In particular, in all examples where carbon dioxide is added in the form of ethyleneurea, the molar ratio of CO to —$NH$-$CH_2$-$CH_2$-$NH$— group is 0.25:1 or lower.

The present invention will be discussed in more detail below.

Monoethylene glycol is used as starting material. This compound can be provided as such, or at least in part in the form of a CO adduct, e.g., in the form of the cyclic ethylene carbonate, or in the form of a linear adduct such as $HO$-$CH_2$-$CH_2$-$O$—$C(O)$—$O$-$CH_2$-$CH_2$-$OH$.

Carbon oxide-delivering agents suitable for use in the present invention are compounds which are able to provide carbonyl groups under reaction conditions. Organic compounds in which a carbonyl group is available include urea and derivatives thereof; linear and cyclic alkylene ureas, especially cyclic urea, mono or di-substituted alkylene ureas, alkyl and dialkyl ureas, linear and cyclic carbamates, organic carbonates and derivatives or precursors thereof. Such derivatives or precursors may for example include ionic compounds such as carbonate or bicarbonate salts that can be converted, in some embodiments in situ in the process of the invention, into their non-ionic counterparts, for example into linear and cyclic carbamate or urea compounds. Preferably, when such ionic compounds are used in the present invention, they are organic hydrocarbon-based carbonate or bicarbonate salts. Preferably, the organic compounds that are suitable for use as carbon oxide-delivering agents are those wherein alkylene is ethylene. The carbon oxide-delivering agent can be present in the process in the same molecule as the amine-functional or the monoethylene glycol compound.

It is preferred for the carbon oxide-delivering agent to be such that it does not provide additional organic compounds to the reaction mixture other than monoethylene glycol and the amine-functional compound.

Accordingly, the carbon oxide-delivering agent used in the present invention includes carbon dioxide, adducts of carbon dioxide with monoethylene glycol, such as the compounds discussed above, and adducts of carbon dioxide with amine-functional compounds.

Examples of suitable carbonyl adducts of amine-functional compounds include ethylene urea (EU), diaminoethylene urea (DAEU), which is the linear carbonyl adduct of two ethylene diamine molecules, the cyclic urea derivative of diethylene triamine (UDETA), and cyclic urea derivatives of triethylene tetramine, such as the cyclic urea derivative of triethylene tetramine, with the carbonyl group added to the terminal NH2-C4H4-NH moiety (U1TETA) and the cyclic diurea additive of triethylene tetramine (DUTETA). In the present specification (U)TETA stands for U1TETA, U2TETA, DUTETA or L-TETA. The sum of all TETA isomers and their urea derivatives is designated by Σ(U)TETAs.

Examples of carbon oxide delivering agents include:

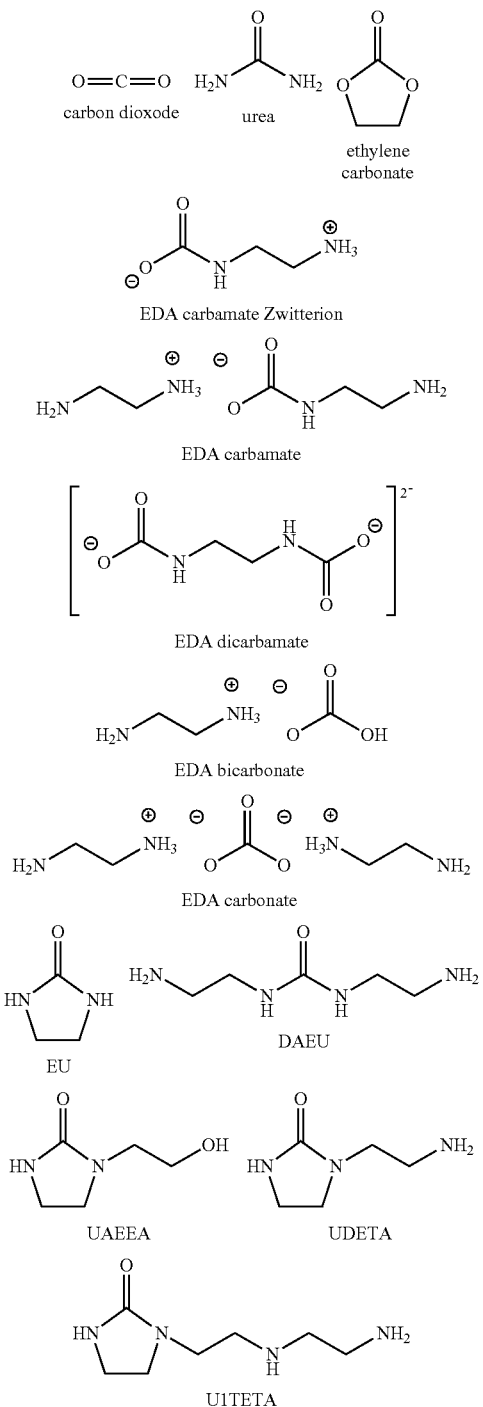

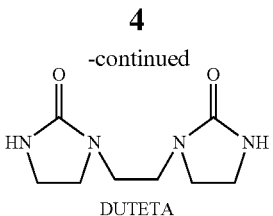

DUTETA

The use of a carbon oxide-delivering agent selected from the group of carbon dioxide, ethylene carbamate, and ethylene urea (EU) and other urea adducts of amine compounds may be particularly preferred. Of course, combinations of the various types of carbon oxide delivering agents may be applied, if so desired.

The present invention makes use of an amine-functional compound as starting material. The amine-functional compound comprises at least two —NH— units of which at least one, in particular two (or more, if more are present), are selected from the group of primary amine groups and cyclic secondary amine groups. Cyclic secondary amine groups can be found in urea derivatives or piperazines. It is preferred in the amine-functional compound for the nitrogen atoms to be connected to each other via an ethylene chain (—CH2-CH2-), via a carbonyl group (—C(O)—), via two ethylene chains (thereby forming a piperazine ring), or via an ethylene chain and a carbonyl group (thereby forming a urea derivative).

Some examples of suitable amine-functional compounds are shown below as illustration. As will be clear to the skilled person, this can be extended to include pentamines, hexamines and so on.

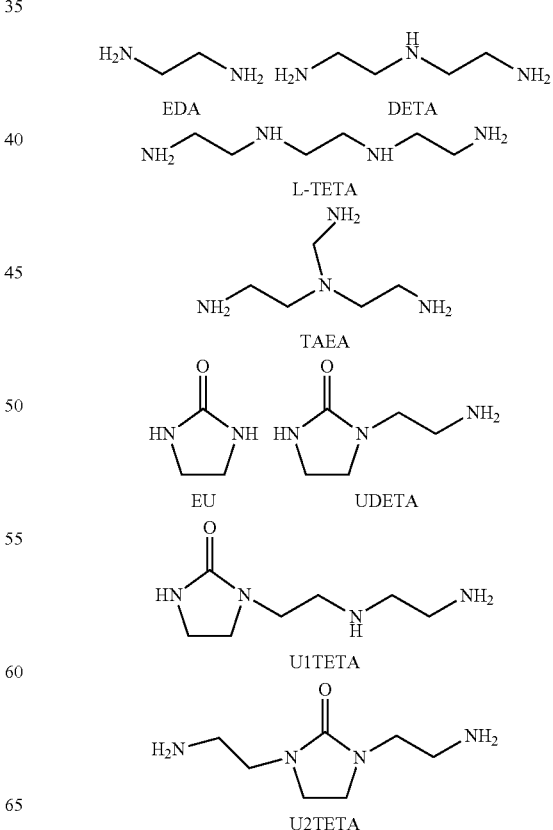

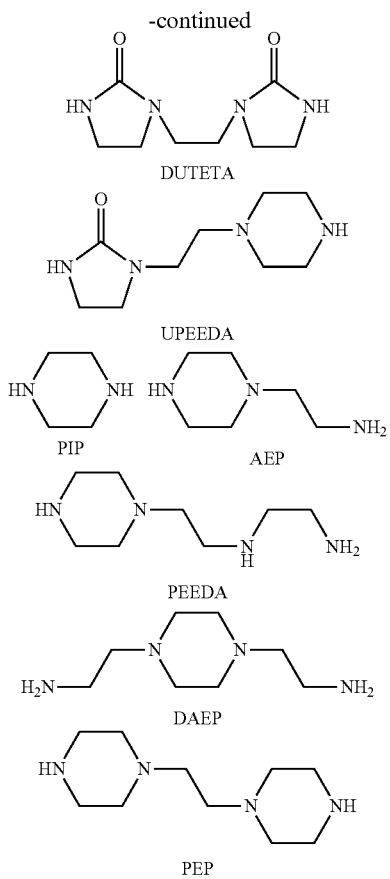

EDA Ethylene diamine
EU Ethylene urea
PIP Piperazine
DETA Diethylene triamine
UDETA Cyclic urea derivative of diethylenene triamine
AEP Aminoethyl piperazine
L-TETA Linear triethylene tetramine
U1TETA Cyclic urea derivative of triethylene tetramine, with the carbonyl group added to the terminal NH2-CH2-CH2-NH moiety
PEEDA Piperazinoethyl ethylene diamine
TAEA Trisaminoethylamine
U2TETA Cyclic urea derivative of triethylene tetramine, with the carbonyl group added to the central NH-CH2-CH2-NH moiety
DAEP Diaminoethyl piperazine
DUTETA Cyclic diurea additive of triethylene tetramine
PEP Piperazinoethyl piperazine
UPEEDA Cyclic urea derivative of piperazinoethyl ethylene diamine In one embodiment, the amine-functional compound comprises at least one —NH-CH2-CH2-NH— unit, wherein the —NH-CH2-CH2-NH— units in the amine-functional compound may be present in the form of a cyclic ethylene urea moiety or a piperazine moiety. EDA, EU, DETA and UDETA may be mentioned as preferred compounds. PIP and AEP may also be attractive. There may be a particular preference for EDA and EU.

In one embodiment, the amine-functional compound and the carbon oxide-delivering agent are to be at least partly added as one compound in the form of a urea adduct.

In the process according to the invention, the molar ratio of amine-functional compound to monoethylene glycol is above 1.2:1. If the molar ratio of amine-functional compound to monoethylene glycol is 1.2:1 or less, the conversion to ethylene amines may be too low due to the formation of hydroxyethylene amine side products. It may be preferred for the molar ratio of amine-functional compound to monoethylene glycol to be above 1.5:1, in particular above 1.7:1.

The maximum for the molar ratio of amine-functional compound to monoethylene glycol is not critical to the present invention. As a general maximum a ratio of 5:1 may be mentioned. It may be preferred for the molar ratio of amine-functional compound to monoethylene glycol to be at most 4:1, in particular at most 3:1.

In the process of the invention the molar ratio of carbon oxide-delivering agent to —NH-CH2-CH2-NH— units in the amine-functional compound is at least 0.5:1. If the value is below this range, the conversion will be too low. It may be preferred for the ratio to be at least 0.7:1, or at least 0.9:1, in some embodiments at least 1:1.

The maximum ratio is not critical. An upper limit of 5:1 may be mentioned in general. A maximum ratio of 3:1 may be attractive in commercial operation. Further, it has been found that an optimum yield can be obtained if the molar ratio of carbon oxide-delivering agent to —NH-CH2-CH2-NH— units in the amine-functional compound is selected to be between 0.7:1 and 3:1, in some embodiments between 0.9:1 and 2:1, specifically between 1:1 and 1.75:1.

In this context a —NH-CH2-CH2-NH— unit is a unit which can form an ethylene urea unit in the amine-functional compound. For example, ethylene diamine (NH2-CH2-CH2-NH2) contains one —NH-CH2-CH2-NH— unit. Diethylene triamine (NH2-CH2-CH2-NH-CH2-CH2-NH2) also contains one —NH-CH2-CH2-NH— unit, since the middle NH unit can be part of only one —NH-CH2-CH2-NH— unit. Triethylene tetramine (NH2-CH2-CH2-NH-CH2-CH2-CH2-NH-CH2-CH2-NH2) contains two —NH-CH2-CH2-NH— units.

In one embodiment, the CO-delivering agent also provides the monoethylene glycol, in the form of ethylene carbonate, as a whole or in part, and/or the CO-delivering agent also provides the amine-functional compound as a whole or in part. It may be preferred to add at least 50% of the CO in the form of either monoethylene glycol or in the form of the amine-functional compound, in particular at least 75%, more in particular at least 90%. In one embodiment, at least 95%, or essentially all, of the CO is added in the form of either monoethylene glycol or in the form of the amine-functional compound.

In this case the maximum molar ratio of the CO-delivering compound to the number of ethylene groups present in the system as monoethylene glycol and —NH-CH2-CH2-NH— units in the amine-functional compound is 1:1.

The process according to the invention can be used to manufacture ethylene diamines, urea and piperazine derivatives thereof, and adducts thereof with CO2.

In one embodiment, the reaction product comprises ethylene amines of the formula $NH_2$—$(CH2-CH2-NH-)_pH$ wherein p is at least 3, or derivatives thereof wherein one or more —NH-CH2-CH2-NH— units may be present as cyclic ethylene urea units

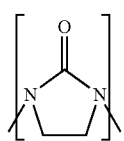

and/or piperazine units

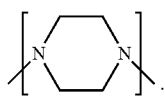

In one embodiment, one or more ethylene amines or derivatives thereof as specified above are connected to each other via a linear ethylene urea structure, e.g. as follows:

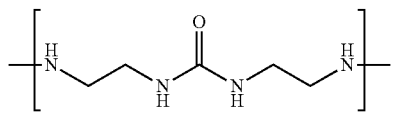

In one embodiment of the present invention, the amine-functional compound comprises ethylene diamine (EDA), ethylene urea (EU), or a mixture thereof, and the reaction product comprises triethylene tetramine (TETA) of the formula NH2-(CH2-CH2-NH-)p-H wherein p is 3, wherein one or more —NH-CH2-CH2-NH— units may be present as cyclic ethylene urea units and/or or piperazine units, wherein one or more ethylene amines or derivatives thereof can be connected to each other via a linear ethylene urea structure.

In one embodiment of the present invention, the amine-functional compound comprises diethylene triamine (DETA), the urea adduct thereof (UDETA), or a mixture thereof, and the reaction product comprises pentaethylene hexamine (PEHA) of the formula NH2-(CH2-CH2-NH-)p-H wherein p is 5, wherein one or more —NH-CH2-CH2-NH— units may be present as cyclic ethylene urea units and/or or piperazine units, wherein one or more ethylene amines or derivatives thereof can be connected to each other via a linear ethylene urea structure.

In one embodiment of the present invention, the amine-functional compound comprises piperazine (PIP) and the reaction product comprises HN(CH2-CH2)2N-CH2-CH2-N(CH2-CH2)2NH.

It should be noted that the relative ratios between the various components are to be calculated based on the compounds monoethylene glycol, carbon dioxide, and amine-functional compound, irrespective of the form in which they are added. For example, one mole ethylene urea should be regarded as being equivalent to one mole carbon dioxide and one mole ethylene diamine. For another example, one mole of the diurea adduct of triethylene tetramine (DUTETA) should be regarded as being equivalent to two moles carbon dioxide-delivering agent and one mole triethylene tetramine.

The reaction is carried out by combining the various components and bringing the mixture to reaction conditions.

Reaction conditions include a reaction temperature which is generally at least 100° C. The temperature should preferably be lower than 400° C. More preferably, the temperature is between 200 and 360° C. Even more preferably, the temperature is between 240 and 340° C. Most preferably, the temperature is between 250 and 310° C. The reaction is carried out at a pressure which is such that the reaction mixture is in the liquid phase. It will therefore depend on the reaction temperature. In general, the reaction pressure will be between 1 and 60 bar.

The reaction time during the process in an embodiment is between 5 minutes and 40 hours, preferably between 0.5 and 10 hours, more preferably between 1 and 6 hours.

The process of the present invention can be performed with or without any additional liquid present. If a liquid is added to the reaction system, the liquid preferably is a polar liquid, such as an alcohol or water. Performing the process of the present invention in the presence of water as a liquid or without any additional liquid is preferred.

The reactor employed can be any suitable reactor including a continuously stirred tank reactor, pipeline reactor, tubular or multi-tubular reactor. The reactor may be adiabatic or equipped with external or internal heating devices. Feed may be single point or split into multiple points. It can consist of multiple stages with inter-stage heat exchange.

The process can be carried out in a batch reactor, possibly fed-batch operation, or in a continuously operating system in one reactor or in a cascade of continuous flow reactors. The reactor can be a single reaction unit or a set of reaction units. The reaction and separation can be performed in separate steps or at least partially simultaneously. The reaction and separation can involve multiple reaction steps with separation steps in between.

In the large-scale production of chemicals it is preferred to employ a continuous process. The continuous process may be, for example, a single-pass or a recycle process. In a single-pass process, one or more of the reagents pass through the process equipment once, and then the resulting effluent from the reactor is sent for purification or further processing.

The person skilled in the art is capable of selecting the proper reactor and separation unit scheme by determining the overall yield, energy consumption and waste production.

The product mixture can be further processed or fractionated into several products that each independently are either pure compounds or mixture of compounds, some of which may be recycled.

The reaction product will comprise one or more compounds in the form of urea adducts. In one embodiment, the product is subjected to a hydrolysis reaction to convert the urea adduct into amine compounds.

The present invention will be elucidated by the following examples, without being limited thereto or thereby.

EXAMPLE 1: MEG+EDA+EU AT DIFFERENT CO:AMINE-FUNCTIONAL COMPOUND MOLAR RATIOS

Reaction mixtures were prepared comprising monoethylene glycol, ethylene diamine and ethylene urea. The molar ratio between amine-functional compound (the total of ethylene diamine and ethylene urea) and monoethylene glycol was 2:1. The amount of ethylene urea was selected such that the molar ratio of CO to amine-functional compounds (EDA+EU) was at the value specified in the table, varying between 0.05:1 and 1.5:1.

The reaction mixtures were brought to a temperature of 270° C. under autogenous pressure, and allowed to react for 5 hours. After the reaction, the reaction mixtures comprised the following amount of (U)TETA compounds, calculated in mole percentage based on the starting amount of MEG in moles.

| Experiment | 1.1 | 1.2 | 1.3 | 1.4 | 1.5 | 1.6 | 1.7 |
|---|---|---|---|---|---|---|---|
| CO:(EDA + EU) molar ratio | 0.05 | 0.25 | 0.5 | 0.75 | 1.0 | 1.25 | 1.5 |
| Σ(U)TETAs | 0.0 | 0.7 | 13.7 | 24.1 | 26.0 | 32.5 | 28.6 |

As can be seen from this data, a CO:(EDA+EU) ratio of 0.05:1 or 0.25:1 is insufficient to obtain a meaningful conversion.

EXAMPLE 2: MEG+EDA+EU AT DIFFERENT REACTION TIMES

Reaction mixtures were prepared comprising monoethylene glycol, ethylene diamine and ethylene urea. The molar ratio between amine compound (the total of ethylene diamine and ethylene urea) and monoethylene glycol was 3:1. The amount of ethylene urea was selected such that the molar ratio of CO to amine-functional compound was at the value specified in the table. Reactions were carried out at 270° C. for 5 hours and for 8 hours. After the reaction, the reaction mixtures comprised the following amount of (U)TETA compounds, determined as GC-FID data in wt. %.

|  | Experiment | | | |
| --- | --- | --- | --- | --- |
|  | 2.1 | 2.2 | 2.3 | 2.4 |
| Reaction time | 5 hours | 8 hours | 5 hours | 8 hours |
| CO:(EDA + EU) molar ratio | 0.83 | 0.83 | 1 | 1 |
| Σ(U)TETAs | 19.0 | 21.9 | 13.4 | 20.9 |

As can be seen from this data, CO:(EDA+EU) molar ratios of 0.83:1 and 1:1 give good results. Longer reaction times lead to increased formation of (U)TETA compounds.

EXAMPLE 3: REACTION AND SUBSEQUENT HYDROLYSIS

A reaction mixture was prepared comprising monoethylene glycol, ethylene diamine and ethylene urea. The molar ratio between amine compound (the total of ethylene diamine and ethylene urea) and monoethylene glycol was 3.5:1. The amount of ethylene urea was selected such that the molar ratio of CO to (EDA+EU) was 2.5:1. Reaction was carried out at 270° C. for 16 hours. The reaction product was contacted with a NaOH solution to hydrolyze the urea groups.

The reaction mixture before hydrolysis contained about 26 wt. % of (U)TETA compounds, all in the form of urea derivatives. After hydrolysis, the reaction mixture contained about 25 wt. % of (U)TETA compounds, with only about 2% in the form of urea derivatives.

EXAMPLE 4: UDETA+CO2 AS STARTING MATERIAL

A reaction mixture was prepared comprising monoethylene glycol, UDETA, and CO2 in a molar ratio of 1:2:2.5 (CO:amine-functional compound molar ratio=2.25:1). CO2 was added in gaseous form. The mixture was reacted at 270° C. for 5 hours under autogenous pressure. The resulting product comprised 43 wt. % of urea derivatives of pentaethylene hexamine.

The invention claimed is:

1. A process for preparing polyethyleneamines of the formula NH2-(CH2-CH2-NH-)pH wherein p is at least 3, comprising the step of reacting monoethylene glycol with an amine-functional compound comprising at least two —NH— units of which at least one is selected from the group of primary amine groups and cyclic secondary amine groups, in the presence of a carbon oxide-delivering agent, the amine-functional compound comprising at least one —NH-CH2-CH2-NH— unit, wherein at least one —NH-CH2-CH2-NH-unit in the amine-functional compound is present in the form of a cyclic ethylene urea moiety of the formula

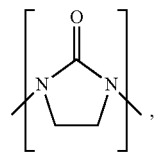

or a piperazine moiety of the formula

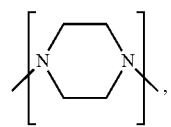

wherein
the molar ratio of amine-functional compound to monoethylene glycol is above 1.2:1 and
the molar ratio of carbon oxide-delivering agent to —NH-CH2-CH2-NH— in the amine-functional compound is at least 0.5:1,
wherein a —NH-CH2-CH2-NH— unit is a unit which can form an ethylene urea unit in the amine-functional compound, and
wherein the carbon oxide delivering agent is selected from the group of carbon dioxide, the CO adduct of monoethylene glycol selected from the group of cyclic ethylene carbonate and HO-CH2-CH2-O—C(O)—O-CH2-CH2-OH, and urea-derivatives of ethylene amine compounds.

2. The process according to claim 1, wherein the carbon oxide-delivering agent is selected from the group of carbon dioxide and ethylene urea (EU) of the formula

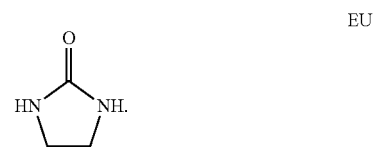

3. The process according to claim 1, wherein the molar ratio of amine-functional compound to monoethylene glycol is above 1.5:1.

4. The process according to claim 1, wherein the molar ratio of carbon oxide-delivering agent to —NH-CH2-CH2-NH— units in the amine-functional compound is at least 0.5:1.

5. The process according to claim 4, wherein the molar ratio of carbon oxide-delivering agent to —NH-CH2-CH2-NH— units in the amine-functional compound is between from 0.7:1 to 3:1.

6. The process according to claim 1, wherein at least 50% of the CO is added in the form of the CO adduct of monoethylene glycol selected from the group of cyclic ethylene carbonate and HO-CH2-CH2-O—C(O)—O-CH2-CH2-OH, or in the form of urea-derivatives of ethylene amine compounds.

7. The process according to claim 1, wherein the amine-functional compound comprises ethylene diamine (EDA) provided in the form of EDA, in the form of the urea derivative ethylene urea (EU) having the formula

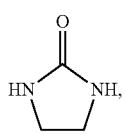

or as a mixture thereof, and the reaction product comprises triethylenetetramine (TETA) of the formula NH2-(CH2-CH2-NH-)p-H wherein p is 3.

8. The process according to claim 1, wherein the amine-functional compound comprises diethylene triamine (DETA) provided as DETA, as the urea adduct thereof (UDETA), or a mixture thereof, and the reaction product comprises pentaethylene hexamine (PEHA) of the formula NH2-(CH2-CH2-NH-)p-H wherein p is 5.

9. The process according to claim 1, wherein the amine-functional compound comprises piperazine (PIP) and the reaction product comprises HN(CH2-CH2)2N-CH2-CH2-N(CH2-CH2)2NH.

10. The process according to claim 1, wherein the reaction product is subjected to a hydrolysis reaction to convert the urea adducts present therein into ethylene amines.

11. The process according to claim 1, wherein the molar ratio of amine-functional compound to monoethylene glycol is above 1.7:1.

12. The process according to claim 1, wherein the molar ratio of amine-functional compound to monoethylene glycol is at most 5:1.

13. The process according to claim 1, wherein the molar ratio of amine-functional compound to monoethylene glycol is at most 3:1.

14. The process according to claim 1, wherein the molar ratio of carbon oxide-delivering agent to —NH-CH2-CH2-NH— units in the amine-functional compound is at least 1:1.

15. The process according to claim 1, wherein the molar ratio of carbon oxide-delivering agent to —NH-CH2-CH2-NH— units in the amine-functional compound is at most 5:1.

16. The process according to claim 1, wherein the molar ratio of carbon oxide-delivering agent to —NH-CH2-CH2-NH— units in the amine-functional compound is at most 3:1.

17. The process according to claim 4, wherein the molar ratio of carbon oxide-delivering agent to —NH-CH2-CH2-NH— units in the amine-functional compound is between from 0.9:1 to 2:1.

18. The process according to claim 4, wherein the molar ratio of carbon oxide-delivering agent to —NH-CH2-CH2-NH— units in the amine-functional compound is between from 1.1:1 to 1.75:1.

19. The process according to claim 1, wherein at least 75% of the CO is added in the form of the CO adduct of monoethylene glycol selected from the group of cyclic ethylene carbonate and HO-CH2-CH2-O—C(O)—O-CH2-CH2-OH, or in the form of urea derivatives of ethylene amine compounds.

20. The process according to claim 1, wherein at least 95% of the CO is added in the form of the CO adduct of monoethylene glycol selected from the group of cyclic ethylene carbonate and HO-CH2-CH2-O—C(O)—O-CH2-CH2-OH, or in the form of urea derivatives of ethylene amine compounds.

* * * * *